US006995729B2

United States Patent
Govari et al.

(10) Patent No.: US 6,995,729 B2
(45) Date of Patent: Feb. 7, 2006

(54) TRANSPONDER WITH OVERLAPPING COIL ANTENNAS ON A COMMON CORE

(75) Inventors: Assaf Govari, Haifa (IL); Andres Claudio Altmann, Haifa (IL); Michael Levin, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 10/754,751

(22) Filed: Jan. 9, 2004

(65) Prior Publication Data

US 2005/0151696 A1 Jul. 14, 2005

(51) Int. Cl.
*H01Q 21/00* (2006.01)
(52) U.S. Cl. ..................................... 343/867
(58) Field of Classification Search .............. 343/867, 343/742; 600/300, 373
See application file for complete search history.

(56) References Cited

U.S. PATENT DOCUMENTS

| | | | | |
|---|---|---|---|---|
| 5,223,851 | A | * | 6/1993 | Hadden et al. .............. 343/873 |
| 5,923,300 | A | * | 7/1999 | Mejia .......................... 343/788 |
| 6,239,724 | B1 | | 5/2001 | Doron et al. |
| 6,261,247 | B1 | | 7/2001 | Ishikawa et al. |
| 6,262,247 | B1 | | 7/2001 | Kaser et al. |
| 6,332,098 | B2 | | 12/2001 | Ross et al. |
| 2002/0165592 | A1 | | 11/2002 | Glukhovksy et al. |
| 2003/0006759 | A1 | | 1/2003 | Govari |
| 2003/0018246 | A1 | | 1/2003 | Govari |
| 2003/0120150 | A1 | | 6/2003 | Govari |
| 2004/0011365 | A1 | * | 1/2004 | Govari et al. ................ 128/899 |
| 2004/0113790 | A1 | * | 6/2004 | Hamel et al. ............. 340/572.1 |
| 2005/0087599 | A1 | * | 4/2005 | Ward et al. .................. 235/451 |

FOREIGN PATENT DOCUMENTS

| | | |
|---|---|---|
| EP | 1374792 A1 | 1/2004 |
| JP | 2003257757 A | 9/2003 |
| WO | WO 00/38571 A1 | 7/2000 |

OTHER PUBLICATIONS

European Search Report EP 05250039 dated Apr. 28, 2005.

* cited by examiner

*Primary Examiner*—Wilson Lee
*Assistant Examiner*—Huedung X. Cao
(74) *Attorney, Agent, or Firm*—Louis J. Capezzuto

(57) ABSTRACT

A wireless device includes an antenna assembly, including a core and one or more power coils, wound around the core on respective power coil axes, including at least a first power coil having a first power coil axis. One or more signal coils are wound around the core on respective signal coil axes, including at least a first signal coil wound so as to overlap the first power coil, the first signal coil having a first signal coil axis that is substantially parallel to the first power coil axis. Power circuitry is coupled to the power coils so as to receive therefrom first radio signals in a first frequency band, and to rectify the first radio signals so as to generate a direct current. Communication circuitry, powered by the direct current, is coupled to perform at least one of transmitting and receiving second radio signals in a second frequency band via the signal coils.

7 Claims, 2 Drawing Sheets

TRANSPONDER WITH OVERLAPPING COIL ANTENNAS ON A COMMON CORE

FIELD OF THE INVENTION

The present invention relates generally to wireless transponder devices, and specifically to miniaturized antenna assemblies for use in such devices.

BACKGROUND OF THE INVENTION

Passive wireless transponders are known in the art. "Passive" in this context means that the transponder includes no internal energy source, such as a battery. Typically, such transponders receive the energy they need to operate by induction from an external radio-frequency (RF) electromagnetic field. For this purpose, the transponder generally comprises both a power antenna, for receiving energy from the field, and a communication antenna, for transmitting and/or receiving communication signals to and/or from an external base station. Such transponders may be used, inter alia, to transmit and receive signals used in determining the location of an object within the body of a patient. Transponders of this sort are described, for example, in U.S. patent application Ser. No. 10/029,473, to Govari, filed Dec. 21, 2001, and published as U.S. 2003/0120150 A1, which is assigned to the assignee of the present patent application, and whose disclosure is incorporated herein by reference.

As another example, U.S. Pat. No. 6,239,724, to Doron et al., whose disclosure is incorporated herein by reference, describes a telemetry system for providing spatial positioning information from within a patient's body. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

PCT patent publication WO 00/38571 A1 and U.S. Pat. No. 6,261,247, to Ishikawa et al., whose disclosures are incorporated herein by reference, describe an anatomical position sensing system using one or more substantially spherical transponders for measuring relative positions and distances. The transponders are capable of receiving and transmitting RF signals, thus communicating between themselves and with a separate CPU. The CPU controls a broadband antenna to transmit a low-frequency RF power signal to energize the transponders. Once energized, the transponders transmit range signals in all directions at other frequencies. These signals are used in determining the positions of the transponders.

In one embodiment described by Ishikawa et al., the transponder is fabricated on a spherical substrate, and includes nine coils in three sets of three coils. Each set is orthogonal to the others and comprises three coils: one transmit coil, one receive coil, and one power coupling coil. The coil sets are grouped in this fashion to ensure that at least one coil set is oriented to provide potentially optimum power coupling and signal communication therewith. Each of the power coupling coils is connected to a power circuit, which rectifies the varying magnetic energy coupled into the coil. The power circuits are connected in series to provide power to the other transponder circuits.

SUMMARY OF THE INVENTION

Embodiments of the present invention provide improved antenna designs for wireless transponders. In these embodiments, an antenna assembly comprises overlapping power coils and communication coils wound on a common core. The power coils comprise at least two coils, and preferably three coils, which are wound over a relatively large area of the core in different, respective directions. Preferably, three power coils are wound over substantially the entire core area in orthogonal directions. This arrangement maximizes the effective area (and thus the inductance) of the coils and ensures that at least one of the power coils will receive energy from an external transmitter, regardless of the orientations of the transmitter and the transponder. The power coils are coupled to power circuits, which rectify the energy received by the power coils and thus provide operating power to a communication circuit, which transmits or receives signals through the communication coils.

Since the power coils are typically wound over most or all of the area of the core in two or three different directions, the communication coils substantially overlap the power coils. Winding the communication and power coils on the same core in this manner, as opposed to using separate cores or a non-overlapping coil arrangement, reduces the size of the antenna assembly that is required in order to achieve a given antenna gain, and thus reduces the size of the transponder as a whole relative to passive transponders known in the art. Typically, the communication coils are wound over only a portion of the area of the core in each winding direction, in order to reduce parasitic effects that would otherwise spoil the resonance quality factor (Q) of the power circuit. For similar reasons, the communication coil that is wound around the core in a given direction is preferably not wound directly over the power coil that is wound in the same direction. Rather, the order of winding the coils on the core is such that another coil, typically a power coil wound in a different direction, intervenes between each communication coil and power coil that are wound in the same direction.

In some embodiments of the present invention, the wireless transponder is used in an electromagnetic position sensing system, typically in order to determine the location of an object to which the transponder is fixed inside the body of a patient.

There is therefore provided, in accordance with an embodiment of the present invention, a wireless device, including:

an antenna assembly, including:
a core;
one or more power coils, wound around the core on respective power coil axes, including at least a first power coil having a first power coil axis; and
one or more signal coils, wound around the core on respective signal coil axes, including at least a first signal coil wound so as to overlap the first power coil, the first signal coil having a first signal coil axis that is substantially parallel to the first power coil axis;

power circuitry, coupled to the power coils so as to receive therefrom first radio signals in a first frequency band, and to rectify the first radio signals so as to generate a direct current; and communication circuitry, powered by the direct current, and coupled to perform at least one of transmitting and receiving second radio signals in a second frequency band via the signal coils.

In some embodiments, the first power coil has a power coil width, and the first signal coil has a signal coil width that is substantially less than the power coil width. Typically, the core includes a polyhedron having a face width, and the first power coil has a first power coil width that is equal to at least about 80% of the face width, while the first signal coil width is less than about 50% of the first power coil width. In one embodiment, the first signal coil width is less than about 20% of the first power coil width.

In disclosed embodiments, the one or more power coils include at least second and third power coils having respective second and third power coil axes, wherein the first, second and third power coil axes are mutually substantially orthogonal. Typically, the one or more signal coils include at least second and third signal coils, having respective second and third signal coil axes that are respectively substantially parallel to the second and third power coil axes. In one embodiment, the power coils and signal coils are wound so that between each pair of the first power coil and the first signal coil, the second power coil and the second signal coil, and the third power coil and the third signal coil, another of the coils, typically another of the power coils, is wound.

Typically, the one or more power coils include at least a second power coil, having a second power coil axis that is substantially non-parallel to the first power coil axis, wherein the second power coil is wound between the first power coil and the first signal coil.

In a disclosed embodiment, the communication circuitry is adapted to receive the second radio signals via the signal coils, and to transmit third radio signals that are indicative of a location of the device, responsively to the second radio signals received by the communication circuitry. The communication circuitry may be coupled to transmit the third radio signals via the power coils.

There is also provided, in accordance with an embodiment of the present invention, apparatus for tracking an object, including:

a power transmitter, adapted to radiate radio frequency (RF) energy toward the object in a first frequency band;

one or more field generators, adapted to generate electromagnetic fields in a second frequency band in a vicinity of the object;

a wireless transponder, adapted to be fixed to the object and including:
an antenna assembly, including:
a core;
one or more power coils, wound around the core on respective power coil axes, including at least a first power coil having a first power coil axis; and
one or more signal coils, wound around the core on respective signal coil axes, including at least a first signal coil wound so as to overlap the first power coil, the first signal coil having a first signal coil axis that is substantially parallel to the first power coil axis;
power circuitry, coupled to the power coils so as to receive therefrom the RF energy in the first frequency band, and to rectify the RF energy so as to generate a direct current; and
communication circuitry, powered by the direct current, and coupled to sense an alternating current flowing in the signal coils due to the electromagnetic fields in the second frequency band, and to transmit output signals indicative of the alternating current; and a signal receiver, adapted to receive the output signals and, responsively to the output signals, to determine coordinates of the object.

Typically, the transponder is adapted to be inserted, together with the object, into a body of a subject, while the power transmitter and the one or more field generators are placed outside the body.

The communication circuitry may be coupled to transmit the output signals via the power coils.

There is additionally provided, in accordance with an embodiment of the present invention, a method for wireless sensing, including:

winding one or more power coils around a core on respective power coil axes, including winding at least a first power coil on a first power coil axis;

winding one or more signal coils around the core on respective signal coil axes, including winding at least a first signal coil so as to overlap the first power coil, the first signal coil having a first signal coil axis that is substantially parallel to the first power coil axis;

coupling power circuitry to receive first radio signals in a first frequency band from the power coils, and to rectify the first radio signals so as to generate a direct current;

coupling communication circuitry to perform at least one of transmitting and receiving second radio signals in a second frequency band via the signal coils; and applying the direct current from the power circuitry to power the communication circuitry.

There is further provided, in accordance with an embodiment of the present invention, a method for tracking an object, including:

fixing a wireless transponder to the object, the wireless transponder including:
an antenna assembly, including:
a core;
one or more power coils, wound around the core on respective power coil axes, including at least a first power coil having a first power coil axis; and
one or more signal coils, wound around the core on respective signal coil axes, including at least a first signal coil wound so as to overlap the first power coil, the first signal coil having a first signal coil axis that is substantially parallel to the first power coil axis;
power circuitry, coupled to the power coils so as to receive therefrom the RF energy in a first frequency band, and to rectify the RF energy so as to generate a direct current; and
communication circuitry, powered by the direct current, and coupled to sense an alternating current flowing in the signal coils due to the electromagnetic fields in a second frequency band, and to transmit output signals indicative of the alternating current;

radiating radio frequency (RF) energy toward the object in the first frequency band so as to supply the RF energy via the power coils to the power circuitry;

generating electromagnetic fields in a second frequency band in a vicinity of the object so as to cause the alternating current to flow in the signal coils; and receiving and processing the output signals transmitted by the transponder so as to determine coordinates of the object.

The present invention will be more fully understood from the following detailed description of the embodiments thereof, taken together with the drawings in which:

DETAILED DESCRIPTION OF EMBODIMENTS

Figure 1:
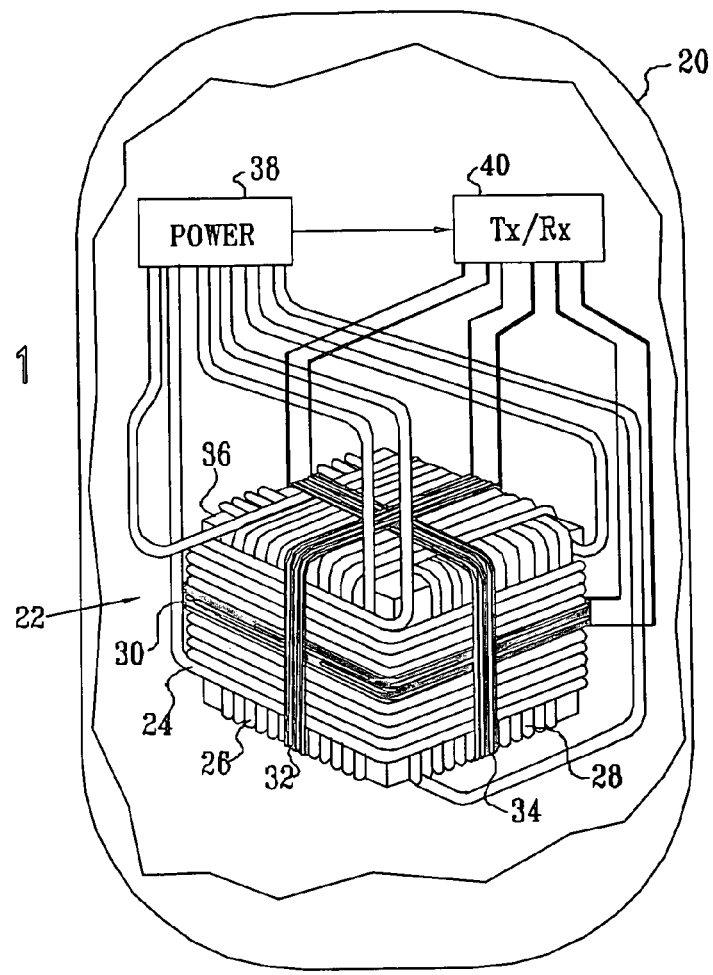
FIG. 1 is a schematic, cutaway illustration of a wireless transponder, in accordance with an embodiment of the present invention.

FIG. 1 is a schematic, cutaway illustration of a wireless transponder 20, in accordance with an embodiment of the present invention. The transponder comprises an antenna assembly, comprising power coils 24, 26 and 28 and communication coils 30, 32 and 34, which are wound on a core 36. Typically, the core comprises a material with high magnetic permeability, such as a ferrite or a Wiegand effect material, as described, for example, in U.S. patent application Ser. No. 09/882,125, to Govari (published as U.S. 2003/0006759 A1), which is assigned to the assignee of the present patent application, and whose disclosure is incorporated herein by reference. Alternatively, core 36 may comprise any other suitable material known in the art. Power coils 24, 26 and 28 typically comprise wires of a relatively large gauge, which are wound over substantially the entire surface of core 36 in mutually-orthogonal directions. Communication coils comprise thinner-gauge wires, and are wound so as to overlap the power coils over only a portion of the surface of the core, typically near the center lines of the faces of the core as shown in the figure.

Power coils 24, 26 and 28 are coupled to a power circuit 38. Typically, the power circuit comprises capacitive elements, coupled to each of the power coils, so as to define resonant circuits. For efficient power transfer from an external RF transmitter (not shown in this figure) to the coils, the resonant circuits are preferably designed to have a sharp resonance (i.e., high Q, typically in the range of about 150) at the transmission frequency of the transmitter, which is typically a permitted ISI frequency, such as 13.56 MHz. Typically, each resonant circuit is coupled to a rectifier, and the rectified outputs are connected in series to give a DC output. The DC output may be regulated in order to maintain a steady output voltage level. A suitable power circuit meeting these general requirements is described, for example, by Ishikawa et al. in the above-mentioned U.S. patent and PCT publication.

Figure 3:
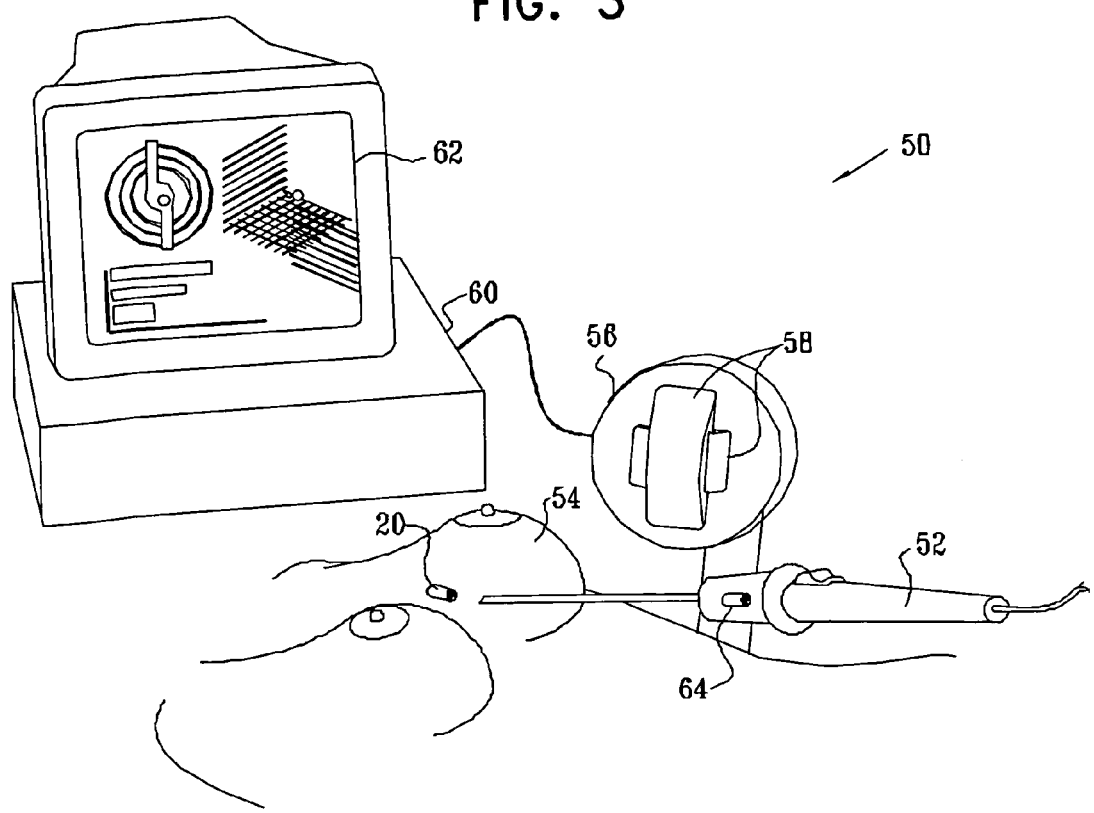
FIG. 3 is a schematic, pictorial illustration of a system for guiding a surgical probe to the location of a wireless transponder in the body of a subject, in accordance with an embodiment of the present invention.

The DC output from power circuit 38 provides operating power to a communication circuit 40. The communication circuit may either transmit or receive signals, or it may both transmit and receive signals, to and from an external receiver and/or transmitter (not shown in this figure). For example, circuit 40 may comprise a transmitter, which is coupled to transmit signals via communication coils 30, 32 and 34. An external receiver may in this case receive and process the signals in order to determine position coordinates of transponder 20. An embodiment of this sort is shown in FIG. 3.

Additionally or alternatively, circuit 40 may comprise a receiver, which receives signals via coils 30, 32 and 34 from one or more external transmitters. For example, these signals may comprise position reference signals, which are transmitted by a set of magnetic field generators in fixed locations at different, respective frequencies, typically in the range of one to several kilohertz. These fields cause currents to flow in coils 30, 32 and 34 by induction. The amplitudes and phases of the currents depend on the spatial position and orientation of coils 30, 32 and 34 relative to the field generators. Communication circuit 40 receives and processes these currents in order to generate signals for transmission to an externally-located signal processing unit (as shown in FIG. 3), which processes the signals to determine position coordinates of transponder 20. For example, the communication circuit may convert the currents from coils 30, 32 and 34 into high-frequency signals. Circuit 40 may transmit the signals to the signal processing unit either via communication coils 30, 32 and 34, or via power coils 24, 26 and 28, or via a further set of transmit coils (not shown), which may be wound on core 36, as well. Exemplary position sensing systems operating on principles similar to these (but without the novel antenna assembly of the present invention) are further described in the above-mentioned U.S. patent application Ser. No. 10/029,473 and U.S. Pat. No. 6,239,724.

Further additionally or alternatively, transponder may comprise another type of sensor (not shown), such as a temperature sensor, a pressure sensor or a chemical sensor, for example. In this case, communication circuit 40 transmits signals via coils 30, 32 and 34 indicating the sensor readings to an external receiver.

Figure 2:
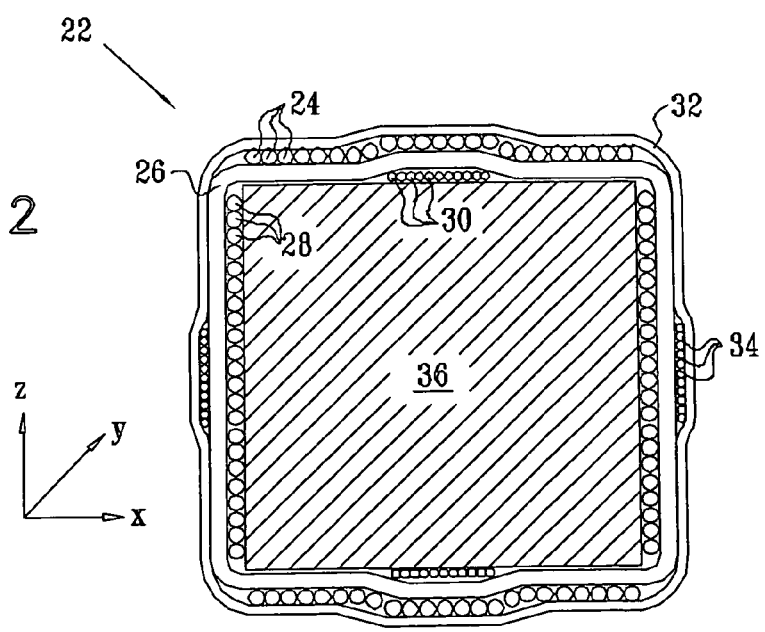
FIG. 2 is a schematic, sectional illustration of an antenna assembly used in a wireless transponder, in accordance with an embodiment of the present invention.

FIG. 2 is a schematic, sectional illustration of antenna assembly 22, in accordance with an embodiment of the present invention. Core 36 is typically polyhedral in shape. In this embodiment, core 36 comprises a cube of ferrite material, with faces that are about 3 mm wide. Alternatively, the core may be round, oval, or of any other suitable shape known in the art. Each of power coils 24, 26 and 28 comprises approximately twenty turns of copper wire, whose diameter is between about 70 and 120 $\mu$m. Comparatively thick wire is used for the power coils because they must carry relatively high power, typically on the order of 5 mW. Communication coils 30, 32 and 34, which carry substantially smaller currents, typically comprise 500 turns of copper wire, with diameter between about 10 and 16 $\mu$m. As shown in the figures, the power coils are wound over substantially the entire width of the core, typically covering at least 80% of each of the faces of the core, and preferably close to 100%. The communication coils, on the other hand, are wound only in the center of each face, typically in a strip about 0.5 mm wide.

Preferably, the width of each of the communication coils is no more than about 50% of the width of the power coil that it overlaps with the same coil axis, and most preferably the communication coil width is no more than about 20% of the width of the power coil. (In the context of the present patent application and in the claims, the term "width," when used in reference to a coil, means the extent of the coil measured along the direction of its axis.) Winding the power coils over substantially the entire core is desirable in order to increase their inductance, and hence to increase the power generated by power circuit 38 relative to the size of assembly 22. Winding the communication coils in a narrower strip reduces their parasitic effect on the power coils. This parasitic effect tends to reduce the Q factor of the resonant power circuits. Alternatively, other winding configurations of the communication coils may be used.

In the present embodiment, the power and communication coils are wound in the following order, beginning from core 36 and moving outward: power coil 28, communication coil 30, power coil 26, communication coil 34, power coil 24 and communication coil 32. In other words, in terms of the coil axis directions shown in the figure, the order is Z-power, X-communication, Y-power, Z-communication, X-power, Y-communication. Each of the communication coils is separated from the power coil with the same axis by at least one other coil, and preferably at least one other power coil. It has been found that this separation is useful in reducing the mutual parasitic effects of the overlapping power and communication coils. Alternatively, other winding orders are possible, for example: Z-power, Y-power, X-power, Z-communication, Y-communication, X-communication.

FIG. 3 is schematic, pictorial illustration of a system 50 for guiding a surgical probe 52 to the location of wireless transponder 20 in a breast 54 of a subject, in accordance with an embodiment of the present invention. In the surgical application shown in this figure, it is assumed that transponder 20 is suitably encapsulated for implantation within the body and was previously implanted in breast 54 at the site of a suspected lesion, typically under radiographic observation. Probe 52 is then used to extract a tissue sample from the site for the purpose of biopsy. Further details of this and other applications of wireless "tags," such as transponder 20, are described in U.S. patent application Ser. No. 10/173,197, to Govari et al. (published as U.S. 2003/0018246 A1), which is assigned to the assignee of the present patent application, and whose disclosure is incorporated herein by reference.

A power transmitter, typically in the form of a power coil 56, generates a high-frequency RF field, which causes a current to flow in at least one of power coils 24, 26 and 28. This current is rectified by power circuit 38 in order to power communication circuit 40. Meanwhile, field generator coils 58 produce electromagnetic fields, typically in the 1–8 kHz range, which cause alternating currents to flow in communication coils 30, 32 and 34. These currents have frequency components at the same frequencies as the driving currents flowing through the generator coils. The current components are proportional to the strengths of the components of the respective magnetic fields produced by the generator coils in a direction parallel to the sensor coil axis. Thus, the amplitudes of the currents indicate the position and orientation of coils 30, 32 and 34 (and hence of transponder 20) relative to fixed generator coils 58.

Circuit 40 encodes the current amplitudes from coils 30, 32 and 34 into a high-frequency signal, which is transmitted via either these coils or via power coils 24, 26 and 28. Alternatively, as noted above, transponder 20 may comprise additional antennas for transmitting signals. The encoded signal is received by coil 56 or by another receiving antenna, and is conveyed to a processing unit 60. Typically, the processing unit comprises a general-purpose computer, with suitable input circuits and software for processing the position signals received over the air from transponder 20. The processing unit computes position and, optionally, orientation coordinates of the transponder, and then shows the tag coordinates on a display 62.

Surgical tool 52 also comprises a position sensor 64, typically comprising one or more coils similar in form and function to coils 30, 32 and 34 in transponder 20. The fields produced by field generator coils 68 also cause currents to flow in sensor 64, in response to the position and orientation of tool 52 relative to coils 68. The current signals thus produced are also conveyed to processing unit 60, either over the air, as in the case of transponder 20, or via wire. Based on the signals from transponder 20 and from sensor 64, processing unit 60 computes the position and orientation of tool 52 relative to the location of the transponder in breast 54. A pointer and/or cursor is shown on display 62 to indicate to the surgeon whether the tool is aimed properly towards its target. Various methods of coordinate display may be used for this purpose, as described, for example, in the above-mentioned U.S. patent application Ser. No. 10/173,197 and U.S. Pat. No. 6,332,098.

Although the embodiment of FIG. 3 is directed to a certain specific surgical procedure, other areas of application of transponder 20 and of the techniques taught by the present invention will be apparent to those skilled in the art. The principles of the present invention may similarly be applied to other types of surgery, including particularly minimally-invasive surgery, endoscopic and non-invasive treatment modalities, and diagnostic procedures, as well as non-medical applications.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for tracking an object, comprising:
   a power transmitter, adapted to radiate radio frequency (RF) energy toward the object in a first frequency band;
   one or more field generators, adapted to generate electromagnetic fields in a second frequency band in a vicinity of the object;
   a wireless transponder, adapted to be fixed to the object and comprising:
      an antenna assembly, comprising:
      a core;
      one or more power coils, wound around the core on respective power coil axes, including at least a first power coil having a first power coil axis; and
      one or more signal coils, wound around the core on respective signal coil axes, including at least a first signal coil wound so as to overlap the first power coil, the first signal coil having a first signal coil axis that is substantially parallel to the first power coil axis;
   power circuitry, coupled to the power coils so as to receive therefrom the RF energy in the first frequency band, and to rectify the RF energy so as to generate a direct current; and
   communication circuitry, powered by the direct current, and coupled to sense an alternating current flowing in the signal coils due to the electromagnetic fields in the second frequency band, and to transmit output signals indicative of the alternating current; and
   a signal receiver, adapted to receive the output signals and, responsively to the output signals, to determine coordinates of the object.

2. The apparatus according to claim 1, wherein the transponder is adapted to be inserted, together with the object, into a body of a subject, while the power transmitter and the one or more field generators are placed outside the body.

3. The apparatus according to claim 1, wherein the first power coil has a power coil width, and wherein the first signal coil has a signal coil width that is substantially less than the power coil width.

4. The apparatus according to claim 1, wherein the one or more power coils comprise at least second and third power coils having respective second and third power coil axes, wherein the first, second and third power coil axes are mutually substantially orthogonal.

5. The apparatus according to claim 4, wherein the one or more signal coils comprise at least second and third signal coils, having respective second and third signal coil axes that are respectively substantially parallel to the second and third power coil axes.

6. The apparatus according to claim 1, wherein the one or more power coils comprise at least a second power coil, having a second power coil axis that is substantially non-parallel to the first power coil axis, wherein the second power coil is wound between the first power coil and the first signal coil.

7. The apparatus according to claim 1, wherein the communication circuitry is coupled to transmit the output signals via the power coils.

* * * * *